United States Patent [19]
Colen

[11] Patent Number: 5,170,806
[45] Date of Patent: Dec. 15, 1992

[54] PROTECTIVE CIRCUIT

[75] Inventor: Fred A. Colen, Ehingen, Fed. Rep. of Germany

[73] Assignee: Lewicki Microelectronic GmbH, Fed. Rep. of Germany

[21] Appl. No.: 611,914

[22] Filed: Nov. 9, 1990

[30] Foreign Application Priority Data

Nov. 10, 1989 [DE] Fed. Rep. of Germany ....... 3937552
Jan. 25, 1990 [DE] Fed. Rep. of Germany ....... 4002187

[51] Int. Cl.$^5$ .............................................. A61N 1/08
[52] U.S. Cl. .................... 128/901; 128/419 PG
[58] Field of Search ............ 128/419 PG, 419 D, 421, 128/908, 901

[56] References Cited

U.S. PATENT DOCUMENTS

| | | | |
|---|---|---|---|
| 3,203,448 | 5/1980 | Keller, Jr. | 128/419 PG |
| 3,795,247 | 3/1974 | Thaler | 128/419 PG |
| 3,796,221 | 3/1974 | Hagfors | 128/419 C |
| 3,968,802 | 7/1976 | Ballis | 128/419 PG |
| 4,290,429 | 9/1981 | Blaser | 128/419 PT |
| 4,320,763 | 3/1982 | Money | 128/419 PG |
| 4,596,252 | 6/1986 | Nelson | 128/902 |
| 4,796,630 | 1/1989 | Regna | 128/908 |

FOREIGN PATENT DOCUMENTS 2133743 1/1972 Fed. Rep. of Germany.
3807503 10/1988 Fed. Rep. of Germany.
3715822 6/1991 Fed. Rep. of Germany.

Primary Examiner—Kyle L. Howell
Assistant Examiner—Kennedy J. Schaetzle
Attorney, Agent, or Firm—Reed Smith Shaw & McClay

[57] ABSTRACT

For the purpose of improving the interference resistance capability of a therapeutically and/or diagnostically operational unit, specifically of a cardiac pacemaker with an input circuit and an output circuit, a decoupling circuit is provided. The decoupling circuit allows the output circuit to be decoupled from the terminal connector pair of the unit. The decoupling of the asymmetrically limiting output circuit always occurs independent of the presence of possible interfering signals for the entire duration of the impulse period.

13 Claims, 4 Drawing Sheets

PROTECTIVE CIRCUIT

FIELD OF THE INVENTION

The invention relates to a protective circuit for the elimination of the influence of continuous, pulsating or modulated interference signals on therapeutic and diagnostic devices, especially cardiac pacer devices.

BACKGROUND OF THE INVENTION

Cardiac pacemakers recognize autonomous cardiac activity by means of an electrode connected to the heart. These electric signals have a low frequency range (up to a maximum of 1 kHz), and have an amplitude varying from about 1 to 10 mV. In order to properly function cardiac pacemakers must not be impaired by a multitude of interfering signals especially when fulfilling their therapeutic function.

There are many currently existing protective circuits which reduce the influx of interfering signals on cardiac pacemakers. One such solution consists in the installation of a capacitor at the terminal connector pair which attenuates interfering signals of higher frequency.

Another solution for the cardiac pacemaker is an electronic circuit located after the input filter and the input amplifier whose switching action stimulates the heart by 100% in the presence of any continuous interfering signal. However, this latter method is achieved at a loss of autonomous cardiac activity detection. A more advanced protective circuit allows the detection of autonomous cardiac activity without switching over to 100% cardiac stimulation during continuous interference.

Cardiac pacemakers presently available which are equipped with the above described circuit variations, however, do not provide sufficient protection against the presence of pulsating or modulating interference signals. Such interfering signals can lead to the suppression of therapeutically indicated impulse stimulation produced by the cardiac pacemaker. In the existing circuit systems, these interfering signals are merely attenuated by an input capacitor and other additional internal filters.

See, e.g., The Institute for Radio Technology in Munich (Institut fur Rundfunktechnik, GmbH, "IRT") reports in EMV, 1988, 545-554 on "The susceptibility of cardiac pacemakers to electric interference caused by powerful radio transmission". This publication lists 34 various types of pacemakers subject to electronic interference. The results show, for example, levels of pacemaker disturbance at an interference voltage ranging from 0.05 V to 2 V at 30 kHz, and an interference voltage of 0.2 V to 17 V at 500 kHz.

The demand for pacemakers with interference elimination is greater than ever. This has been demonstrated by DIN/VDE- and CENELEC in their discussions and studies on standardization. The IRT in Munich requires, for example, a pacemaker disturbance voltage resistance capability of at least 16 V, also for modulated and pulsating interference signals in the frequency range from 30 kHz to 30 MHz. Accordingly, it is an objective of the present invention to provide a protective circuit which will simply meet present requirements of disturbance voltage strength.

SUMMARY OF THE INVENTION

Generally, the present invention provides protection against interfering signals by utilizing a decoupling circuit between the output circuit of the pacemaker and the terminal connector pair. The decoupling circuit of the present invention preferably includes a first series connection with a diode and the collector-emitter line of a transistor between said output circuit and one terminal connector and the base of the transistor is connected, via a base resistor, to the other terminal connector.

In accordance with a preferred embodiment, a second series connection is made between both terminal connectors. This connection consists of a diode and the collector-emitter circuit of a second transistor where the base of the second transistor is regulated by a monostable sweep stage. The monostable sweep stage is activated by the emission of impulses from the output circuit.

The basis of the invention lies in that the asymmetrically limiting output circuit of cardiac pacemaker, normally integrated in a chip, is decoupled from the terminal connector pair of the cardiac pacemaker by a symmetrically limiting circuit. This total decoupling of the asymmetrically limiting output circuit always occurs for the entire duration of the impulse period, and is also independent of the presence of any possibly occurring interference signals. The symmetrically limiting decoupling circuit allows the continuance of impulse transmission from the output circuit and causes the discharge of possibly occurring load capacitances within a brief time interval after the impulse. The decoupling circuit is not in the least regulated by the possible presence of occurring interference signals. Thus the interference signals never reach the asymmetrically limiting output circuit and cannot be demodulated by the symmetrically limiting decoupling circuit. Therefore, the attenuation of these higher frequency interference signals at the pacemaker terminal connector pair by use of a capacitor for reduction of this demodulation in the asymmetrically limiting output circuit is not necessary. Instead, the present higher frequency continuous or also pulsating and modulated interference signals of more than 1 kHz are systematically and powerfully attenuated in the input circuit, so as not to interfere with the intended therapeutic operational activity of the pacemaker.

Furthermore, with the application of adequate circuit components for the decoupling network and the remainder of the pacemaker, there is no need for voltage limitation at the point of the pacemaker terminal connector pair.

In pacemakers where it is not possible to omit a voltage limiter at the point of the terminal connector pair, then a symmetrical input voltage limitation can be installed in the form of a two-way Zener diode.

In accordance with a preferred embodiment, a diode which is placed before the transistor in series connection is set relative to its forward direction, counter to the forward direction of the collector diode of the transistor connected to it. Preferably, the base of the transistors is maintained at a constant potential, relative to high frequency, via capacitors.

In accordance with a preferred embodiment, one terminal connector serves as an impulse output for the negative impulses and the anode of a first diode and the cathode of a second diode are connected to the impulse output terminal. The cathode of the first diode is connected to the collector of a first transistor whose emitter is connected to the impulse output of the output circuit and whose base is connected to the other terminal connector via a first base resistor. The anode of the second diode is then connected to the collector of a second transistor whose emitter is connected to the other terminal connector, and whose base, via a second base resistor, is connected to the output of a monoflop connecting on the entry side to the impulse output of the output circuit. In this embodiment the first transistor consists of an npn transistor, and the second transistor consists of a pnp transistor.

Preferably, the decoupling circuit is decoupled on equal direct current voltage at the impulse output terminal by means of a coupling capacitor.

In accordance with a preferred embodiment, the diodes are Shottky diodes with low forward voltage, and the transistors have a high current amplification factor.

In accordance with another preferred embodiment, the first and second transistors consist of FET transistors.

In accordance with the invention, the protective circuit is specifically suited for cardiac pacemakers of all types, e.g., unipolar bipolar and multipolar cardiac pacemakers, as well as for multiple chamber systems. The protective circuit of the present invention is especially applicable to programmable, detector or sensor controlled, and adaptable cardiac pacemaker systems. Other advantages of the present invention will become apparent from a perusal of the following detailed description a presently preferred embodiment taken in connection with the accompanying drawings.

PRESENTLY PREFERRED EMBODIMENTS

Figure 1:
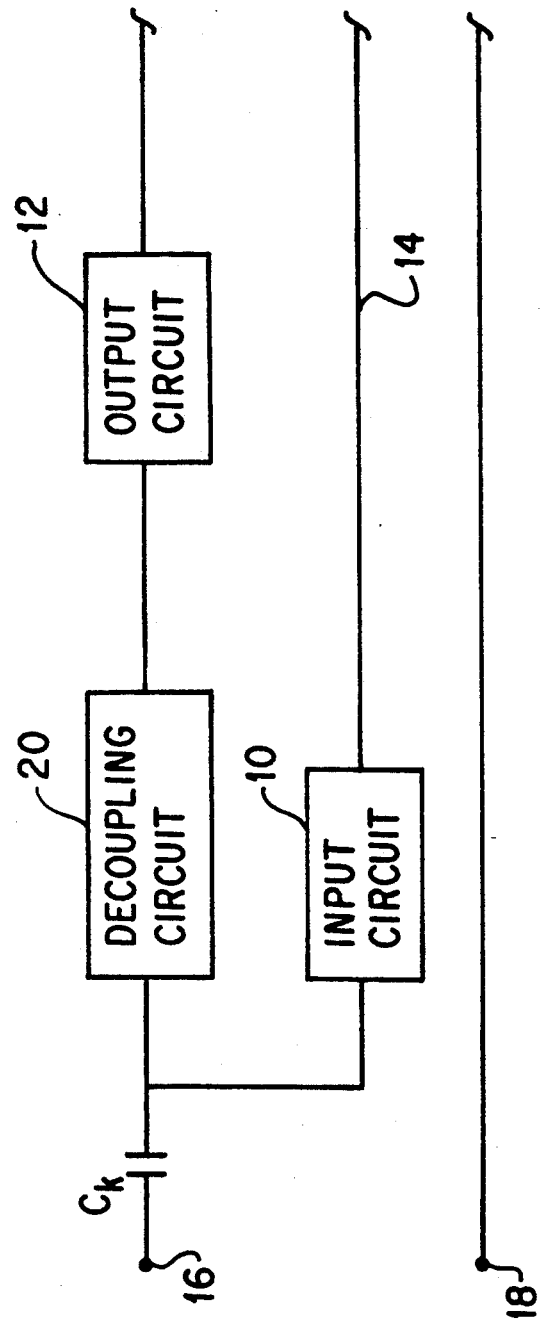
FIG. 1 is a block diagram of a cardiac pacemaker.

Referring to FIG. 1, the circuit of a cardiac pacemaker is illustrated and includes input circuit 10 and output circuit 12. Input circuit 10 is connected to a detector (not shown) via line 14. A decoupling circuit 20 is provided between output circuit 12 and terminal connector pair 16 and 18.

Figure 2:
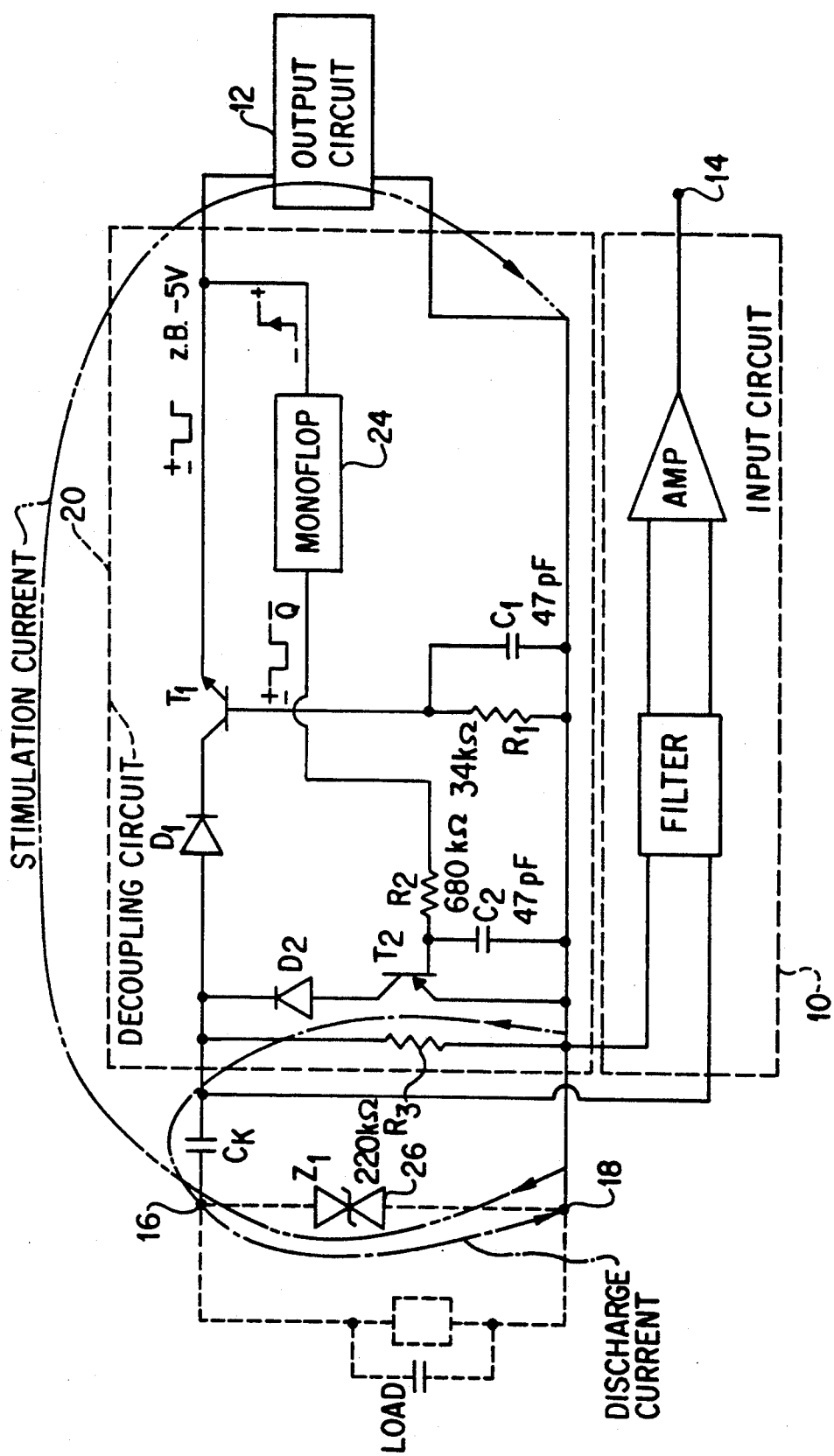
FIG. 2 is a circuit diagram of a decoupling circuit of the present invention.

With reference to FIG. 2, decoupling circuit 20 is shown in greater detail.

Terminal connector 16 serves as an impulse stimulation output for negative stimulation impulses. The anode of a first diode D1 and the cathode of a second diode D2 are connected to impulse output terminal 16. The cathode of first diode D1 is connected to the collector of a first transistor T1 whose emitter is connected to the impulse stimulation output of output circuit 12. The base of transistor T1 is connected to the other terminal connector 18 via first base resistor R1. The anode of second diode D2 is connected to the collector of a second transistor T2 whose emitter is connected to the other terminal connector 18. The base of transistor T2 is connected to the output of monoflop 24 via second base resistor R2. Monoflop 24 is connected on the entry side to the impulse stimulation output of output circuit 12. In this embodiment, first transistor T1 consists of an npn transistor, and the second transistor T2 consists of a pnp transistor.

The decoupling circuit comprises two diodes D1 and D2, each of which operates with transistors T1 and T2 in series connection, respectively. The circuits originating from the diodes and the transistors cause a complete blocking off of external signals of any kind. This is effected in each branch by the blocked collector diode of the transistor and by the counter directional setup of the series diode. The capacitors C1 and C2 provide for the AC decoupling of the base of the transistors T1, T2.

The need to control both transistors past the inevitable parasitic disturbances is thereby circumvented in the case of higher frequency interference signals. This also assures that higher frequency interfering signals will also not reach the asymmetrically limiting output circuit. These are educted over the parasitic capacitance of both diodes D1, D2, by the collector base capacitance of both transistors T1, T2, and by the capacitors C1, C2. In this process, the load of these higher frequency interfering signals on the cardiac pacemaker is considerably less than that of prior art pacemaker circuits with one capacitor (CEMI) on the pacemaker terminal connector pair. The input capacitance of a decoupling circuit amounts to a maximum of 30 pF, as opposed to the usual CEMI-value of 1 to 10 pF.

The negative stimulation impulse of the output circuit is led through the conducting transistor T1 and then through the diode D1, which then operates in forward direction, to the terminal connector 16 of the pacemaker. During this process, the impulse itself opens the transistor T1. As soon as the stimulation impulse is terminated by the impulse duration determination of the pacemaker, then thereafter, with the immediate closing of the transistor T1, the connection between the terminal connector 16 of the pacemaker and the output circuit 12 is interrupted again.

The output amplitude is solely diminished by the voltage drop in the opened transistor T1 and the voltage drop in the forward direction driven diode D1. If the utilized diode is a Shottky diode with low forward voltage, along with a transistor (T1) having a high current amplification factor, it is possible to further limit this output voltage reduction to about 0.3 V with an additional use of current of less than 0.1 $\mu$A (at 5 V amplitude, 0.5 ms impulse duration, 833 ms duration of stimulation period, and a resistance R1 of 34 kOhms).

Immediately after the termination of the stimulation impulse follows the discharge of the coupling capacitor CK and the discharge of possible load capacitances by way of transistor T2 and diode D2. Following the stimulation impulse, transistor T2 opens for a specific discharge duration (normally less than 100 ms), allowing the necessary discharge current to flow through T2 and diode D2, now driven in forward direction. If a Shottky diode with low forward direction voltage is utilized for diode D2, and a transistor T2, having a high current amplification factor, then even in the case of stimulation impulses with high energy levels the discharge of the capitance is ensured with an additional use of current of about 0.2 $\mu$A (at 833 ms duration of stimulation period, 64 ms discharge time, and a resistance R2 e.g., 680 kOhms). During this timespan (duration of stimulation impulse and discharge time) the possible demodulation of interfering signals is of no importance, because the cardiac pacemaker always has an absolute refraction index of at least 100 ms after each emitted stimulation impulse, during which time the possibly occurring signals in the input circuit 10 are not evaluated. A resistor R3, e.g., 220 kOhms, connected in parallel to the diode D2 and the transistor T2 effects, to the extent required, the gradual discharging of residual capacitance and accordingly essentially determines the pacemaker's impedance in the low frequency range (less than 1 kHz).

The input signals are duly filtered in input circuit 10 before they reach amplifier 22 in the input circuit. Higher frequency interfering signals (of more than 1 kHz) are powerfully attenuated by two successive RC low-pass filters. The heart signals, on the other hand, reach input amplifier 22 almost unattenuated.

A corresponding decoupling circuit 20 can also be provided using FET transistors. For this embodiment transistor T1 is replaced by an N-channel MOSFET (source at output circuit 12, drain at diode D1), and transistor T2 is replaced by a P-channel MOSFET (source at terminal connector 18, drain at diode D2). Resistor R1 and capacitor C1 can be omitted in this embodiment, because the gate of transistor T1 can be directly connected at terminal connector 18. It would also be possible to omit resistor R2 and capacitor C2, because the gate of transistor T2 can be directly connected at output $\overline{Q}$ of monoflop 24. Furthermore, this circuit has the advantage of using much less current, due to the omission of the base currents of bipolar transistors T1 and T2.

Decoupling circuit 20 can be totally or partially monolithically integrated into a pacemaker IC, or it can be incorporated into the existing output circuit, and thus either integrated as a discrete design or totally partially monolithically integrated.

If a voltage limiter cannot be omitted at the pacemaker terminal connector pair 16, 18, then a symmetrical input voltage limitation can be installed in the form of a two-way Zener diode 26.

Figure 3:
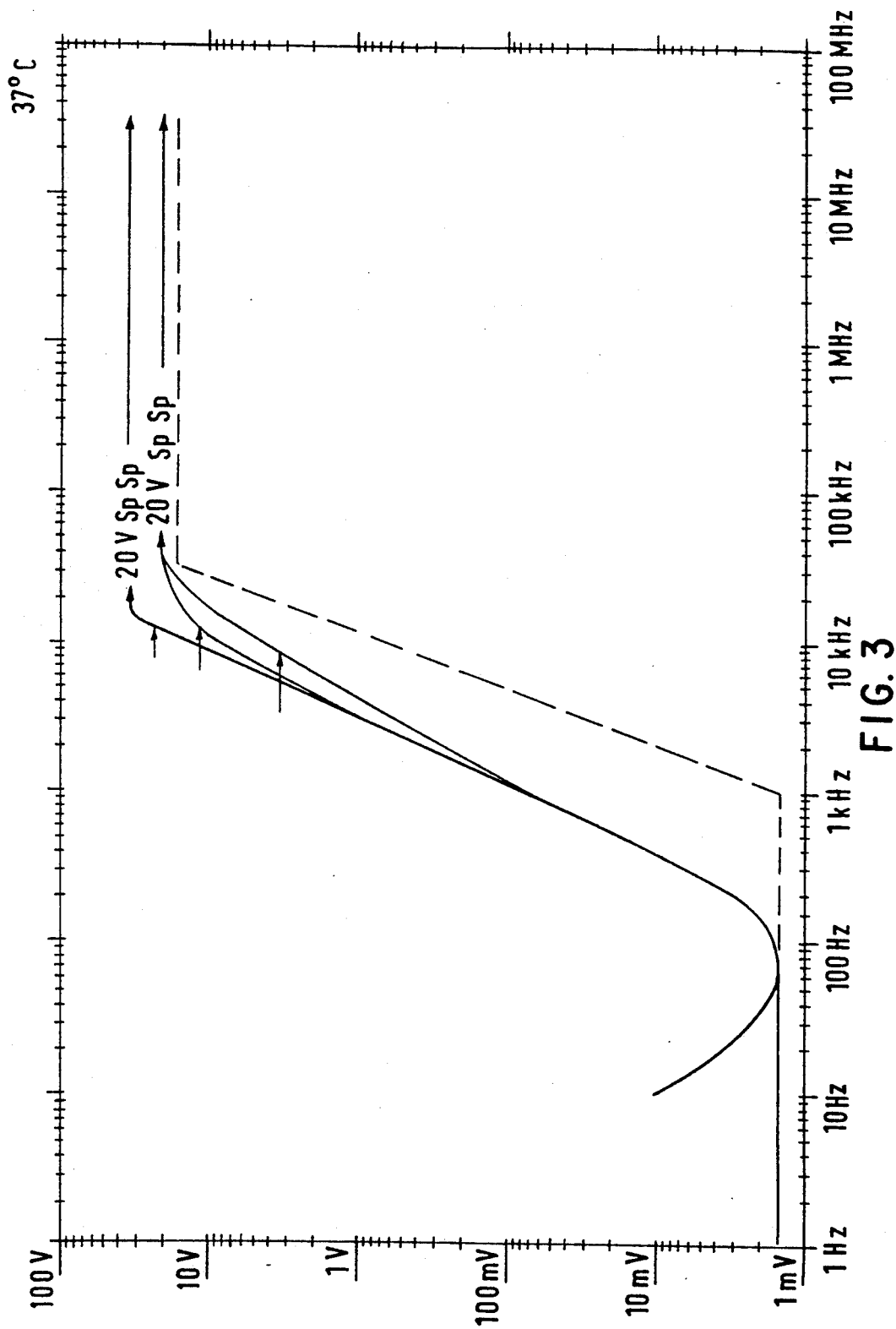
FIG. 3 is a graphic representation of the interference strength of a cardiac pacemaker with a decoupling circuit of the present invention.
Figure 4:
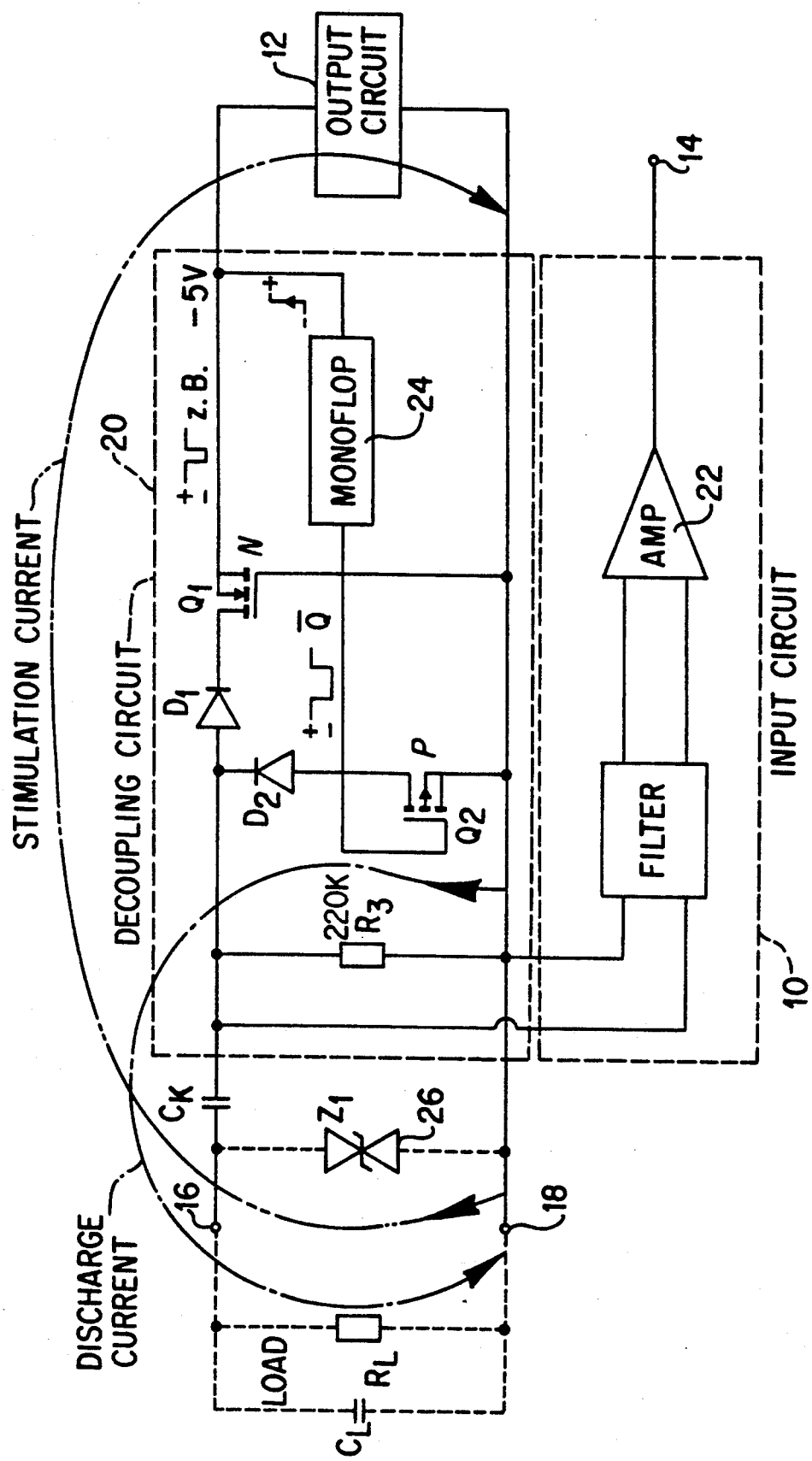
FIG. 4 is a circuit diagram of a decoupling circuit of the present invention including FET transistors.

Measured values of continuous, pulsating, modulated and pulse-modulation (for example with 100% amplitude modulation) interference signals in a modern, completely integrated, multiprogrammable cardiac pacemaker (with telemetry) and decoupling circuit/input circuit, as described above, are illustrated in FIG. 3, and show that:

(a) A demodulation at the cardiac pacemaker terminal connector pair does not occur for the entire frequency range.
(b) None of the higher frequency interfering signals (including pulsating modulated, and pulse-modulation signals) have an influence on the cardiac pacemaker's intended therapeutic operation (the threshold of influence is higher than 16 V for all interfering signals in the frequency range of 30 kHz to 30 MHz, increasing at about 12 dB/octave from 300 Hz to 30 kHz).
(c) The input impedance of the cardiac pacemaker on the frequency remains relatively high-ohmic and amounts to about 200 kOhms in the cardiac signal frequency range (less than 1 kHz), about 50 kOhms at 10 kHz, about 22 kOhms at 100 kHz, and about 500 Ohms at 10 MHz.

A comparison to a cardiac pacemaker without a decoupling circuit shows that:

(a) The low frequency demodulation product of the cardiac pacemaker at the terminal connector pair is reduced from about 1 V to less than 1 mV (carrier frequency 500 kHz, amplitude 20 V peak—peak, modulation frequency 50 Hz, degree of modulation 100% AM, generator with 50 Ohms output impedance over 100 Ohms connected to cardiac pacemaker).
(b) The resistance to interference is considerably improved. For example, for 100% pulsating amplitude modulated interfering signals it is improved by a factor of 20 (carrier frequency between 30 and 100 kHz).
(c) The input impedance of a pacemaker with a decoupling circuit is usually higher:
at 100 Hz, higher by a factor of 4
at 10 kHz, higher by a factor of 30
at 100 kHz, higher by a factor of 100
at 10 MHz, higher by a factor of 250

The decoupling circuit in accordance with the invention offers the following possibilities:

(1) Any cardiac pacemaker equipped with a decoupling circuit conforming to this invention undergoes significant improvement relative to its interference resistance capability, i.e. to interfering signals of all kinds with frequencies of more than 1 kHz. The decoupling circuit can also be adapted to implement existing cardiac pacemakers.
(2) Currently permitted, maximal electric and magnetic continuous field intensities, starting at 30 kHz (DIN/VDE 0848, Part 2, August 1986) will not affect the intended therapeutic operation of any cardiac pacemaker which uses a decoupling circuit in accordance with the invention.
(3) The influence threshold of a cardiac pacemaker for continuous and for pulsating, modulated and pulse-modulation interference signals is many times increased. Due to the omitted demodulation at the output circuit and due to the systematic powerful attenuation of these interference signals versus the heart signal in the input circuit, the operation of a cardiac pacemaker equipped with the decoupling circuit is undisturbed by the presence of continuous, pulsating, modulated or pulse-modulation interference signals. (See FIG. 3).
(4) A demodulation of interfering signals of any kind over the entire frequency range is locked out at the terminal connector pair of a cardiac pacemaker with a decoupling circuit.
(5) Thus, cardiac palpitations induced by demodulation of interfering signals at the cardiac pacemaker's terminal connector pair are eliminated.
(6) The input impedance (as a function of frequency) of a cardiac pacemaker can be drastically increased by the omission or the reduction of capacitance directly at the point of the cardiac pacemaker's terminal connector pair.
(7) The magnitude of the interfering current flowing through the cardiac pacemaker's terminal connector pair is drastically reduced due to the increase in input impedance.
(8) The drastic reduction of interfering current thus eliminates the danger of tissue burns.
(9) All of the above described statements are valid for implants, which exhibit an output circuit and an input circuit for the reception of therapeutically and/or diagnostically significant low frequency heart signals.
(10) Excluding 5, above, all of the above advantages are valid for implants exhibiting an output circuit and an input circuit for the reception of therapeutically and/or diagnostically significant low frequency signals.
(11) The advantages pointed out at 4 and 5 are valid for implants having an output circuit and that are connected to the heart.

(12) The advantage identified in paragraph 4 can be maintained for implants exhibiting an output circuit.

(13) The advantages set forth at 1 through 8 are valid for external therapeutically and diagnostically operational units exhibiting an output or an input circuit connected to the heart for the purpose of receiving therapeutically and/or diagnostically significant low frequency heart signals.

(14) Excluding the statement made in number 5, statements number 1 through 8 are valid for external therapeutically and/or diagnostically operational units exhibiting an output or an input circuit connected to the body for the purpose of receiving therapeutically and/or diagnostically significant low frequency signals.

(15) The advantages stated under paragraphs 4 and 5 are valid for external therapeutically and/or diagnostically operational units exhibiting an output circuit connected to the heart.

(16) A demodulation of interference signals of any kind over the entire frequency range is locked out at the terminal connector pair of an external therapeutically and/or diagnostically operational unit exhibiting an output circuit with a decoupling circuit connected to the body.

Numerous modifications may be made to the described embodiments and other arrangements may be devised without departing from the spirit and scope of the invention. It will be understood that the above description of the present invention is susceptible to various modifications, changes and adaptations, and the same are intended to be comprehended within the meaning and range of equivalents of the appended claims.

What is claimed is:

1. A protective circuit to eliminate or substantially eliminate interference due to continuous, pulsating or modulated interference signals for use in therapeutic and diagnostic devices having an output circuit for producing pulses and first and second output terminal connectors, the protective circuit comprising:
    a first diode means including an anode and a cathode for permitting current to flow in substantially one direction;
    a first transistor means including an emitter, a collector and a base for conducting or blocking said current, wherein said first diode means and said emitter and collector of said first transistor means are adapted to be connected in series between said output circuit and said first output terminal connector;
    a first base resistor connected to said base of said first transistor means and adapted to be connected to said second output terminal connector;
    a second diode means including an anode and a cathode for permitting said current to flow in substantially one direction;
    a second transistor means including an emitter, a collector and a base for conducting or blocking said current, wherein said second diode means and said emitter and collector of said second transistor means are adapted to be connected in series between said first and second output terminal connectors;
    a monostable sweep stage having an input side and an output side; and
    a second base resistor connected to said base of said second transistor means and connected to the monostable sweep stage, wherein said monostable sweep stage is adapted to be connected to said output circuit and is activated by pulses provided by said output circuit.

2. A protective circuit in accordance with claim 1, wherein the forward direction of said first diode means placed before said first transistor means is set counter to the forward direction of the collector of said first transistor means; and
    the forward direction of said second diode means placed before said second transistor means is set counter to the forward direction of the collector of said second transistor means.

3. A protective circuit in accordance with claim 1, including first and second capacitors connected to the base of said first and second transistors means, respectively, and said second output terminal connector whereby said first and second transistor means lie on a constant high frequency potential.

4. A protective circuit in accordance with claim 1, wherein said first output terminal connector transmits negative pulses, said anode of said first diode means is connected to said first output terminal connector, said cathode of said first diode means is connected to said collector of said first transistor means, said emitter of said first transistor means is adapted to be connected to an impulse output of said output circuit, said base of said first transistor means is connected to said second output terminal connector through said first base resistor, and said first transistor means is an npn transistor.

5. A protective circuit in accordance with claim 4, wherein said cathode of said second diode means is connected to said first output terminal connector, said anode of said second diode means is connected to the collector of said second transistor means, said emitter of said second transmitter means is connected to the second output terminal connector, said base of said second transistor means is connected through said second base resistor to said output side of said monostable sweep stage, said monostable sweep stage is connected at its input side to the impulse output of said output circuit, and said second transistor means is a pnp transistor.

6. A protective circuit in accordance with claim 1, wherein said first output terminal connector transmits positive pulses, said cathode of said first diode means is connected to said first output terminal connector, said anode of said first diode means is connected to said collector of said first transistor means, said emitter of said first transistor means is adapted to be connected to an impulse output of said output circuit, said base of said first transistor means is connected to said second output terminal connector through said first base resistor, and said first transistor means is a pnp transistor.

7. A protective circuit in accordance with claim 6, wherein said anode of said second diode means is connected to said first output terminal connector, said cathode of said second diode means is connected to the collector of said second transistor means, said emitter of said second transistor means is connected to said second output terminal connector, said base of said second transistor means is connected through said second base resistor to said output side of said monostable sweep stage, said monostable sweep stage is connected at its input side to said impulse output of said output circuit, and said second transistor means is an npn transistor.

8. A protective circuit in accordance with claim 1 wherein said protective circuit is decoupled at said first terminal connector to eliminate direct current flow, and further includes a coupling capacitor placed between the first output terminal connector and said first and second diode means.

9. A protective circuit in accordance with claim 1, wherein said first and second diode means are Scottky diodes having low forward voltage, and said first and second transistor means have a high current amplification factor.

10. A protective circuit in accordance with claim 1, wherein a symmetrical input voltage limitation means is added between said first and second output terminal connectors.

11. A protective circuit in accordance with claim 10, wherein the symmetrical input voltage limitation means includes a two-way Zener diode placed between the first and second output terminal connectors so as to achieve the symmetrical input voltage limitation.

12. A protective circuit in accordance with claim 1, wherein the protective circuit is entirely or partially monolithically integrated.

13. A protective circuit to eliminate or substantially eliminate interference due to continuous, pulsating or modulated interference signals for use in therapeutic and diagnostic devices having an output circuit for producing pulses and first and second output terminal connectors, the protective circuit comprising:
- a first diode means including an anode and a cathode for permitting current to flow in substantially one direction;
- a first FET transistor means for conducting or blocking said current, wherein said first diode means and said first FET transistor means are adapted to be connected in series between said output circuit and said first output terminal connector;
- a second diode means including an anode and a cathode for permitting said current to flow in substantially one direction;
- a second FET transistor means for conducting or blocking said current, wherein said second diode means and said second FET transistor means are adapted to be connected in series between said first and second output terminal connectors; and
- a monostable sweep stage having an input side and an output side wherein said monostable sweep stage is adapted to be connected to said output circuit and is activated by pulses provided by said output circuit.

* * * * *